United States Patent [19]

Adams et al.

[11] Patent Number: 5,079,728
[45] Date of Patent: Jan. 7, 1992

[54] METHOD AND APPARATUS FOR QUANTITATIVELY EVALUATING ROLL HARDNESS

[75] Inventors: Richard J. Adams; Scott A. Baum, both of Rockton, Ill.; David R. Roisum, Neenah, Wis.; William K. Oliver, Rockton, Ill.

[73] Assignee: Beloit Corporation, Beloit, Wis.

[21] Appl. No.: 472,780

[22] Filed: Jan. 31, 1990

[51] Int. Cl.$^5$ ............................................. G01N 3/30
[52] U.S. Cl. ................................... 364/556; 364/508; 73/12
[58] Field of Search .......... 364/556, 508, 505, 571.01, 364/471; 73/78, 81, 159, 12

[56] References Cited

U.S. PATENT DOCUMENTS

| | | | |
|---|---|---|---|
| 2,737,048 | 3/1956 | Van Erp | 73/79 |
| 2,834,202 | 5/1958 | Cook | 73/81 |
| 3,425,263 | 2/1969 | Elliott et al. | 73/12 |
| 3,425,267 | 2/1969 | Pfeiffer | 73/78 |
| 3,540,270 | 11/1970 | Wolfer | 73/78 |
| 3,822,588 | 7/1974 | Knight et al. | 73/81 |
| 3,879,982 | 4/1975 | Schmidt | 73/12 |
| 4,034,603 | 7/1977 | Leeb et al. | 73/12 |
| 4,534,206 | 8/1985 | Kiso et al. | 73/82 |
| 4,542,639 | 9/1985 | Cawley et al. | 73/12 |
| 4,615,209 | 10/1986 | Change, Jr. | 73/12 |
| 4,856,318 | 8/1989 | Hogan et al. | 73/12 |

FOREIGN PATENT DOCUMENTS 1001230 10/1951 France.

OTHER PUBLICATIONS

Proceq Pamphlet, "Reinforcement Detector Profometer", no date; distributed by Proceq SA Switzerland.
Beloit RhoMeter TM Digital Display Roll Hardness Tester brochure, no Date.

*Primary Examiner*—Thomas G. Black
*Assistant Examiner*—Ellis B. Ramirez
*Attorney, Agent, or Firm*—Leydig, Voit & Mayer

[57] ABSTRACT

A method and apparatus for testing the hardness of wound rolls, such as paper rolls, which yields quantitative information which is reproducible from roll to roll and under various conditions of testing. The apparatus can be operated much like a backtender's stick, to simply strike the roll at a point where hardness is to be determined with a force variable between certain limits as determined by the operator using the stick. The apparatus includes an accelerometer mounted in a striker associated with circuitry for producing signals relating to (a) the energy of the impact between the striker and roll and (b) the peak deceleration of the striker. Those signals are processed to produce a roll hardness measure, which can be correlated to a commonly used Rho scale if desired, and which is repeatable irrespective of the force used by the operator to cause the impact.

17 Claims, 3 Drawing Sheets

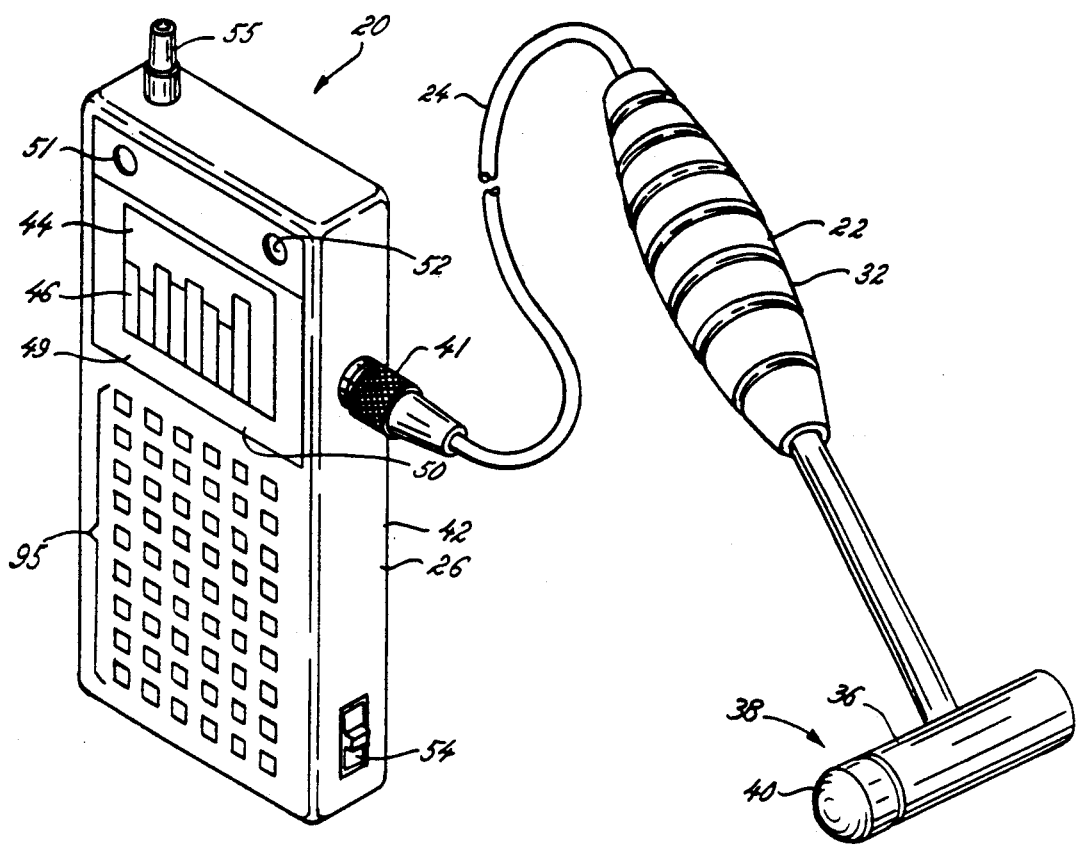
FIG. 1
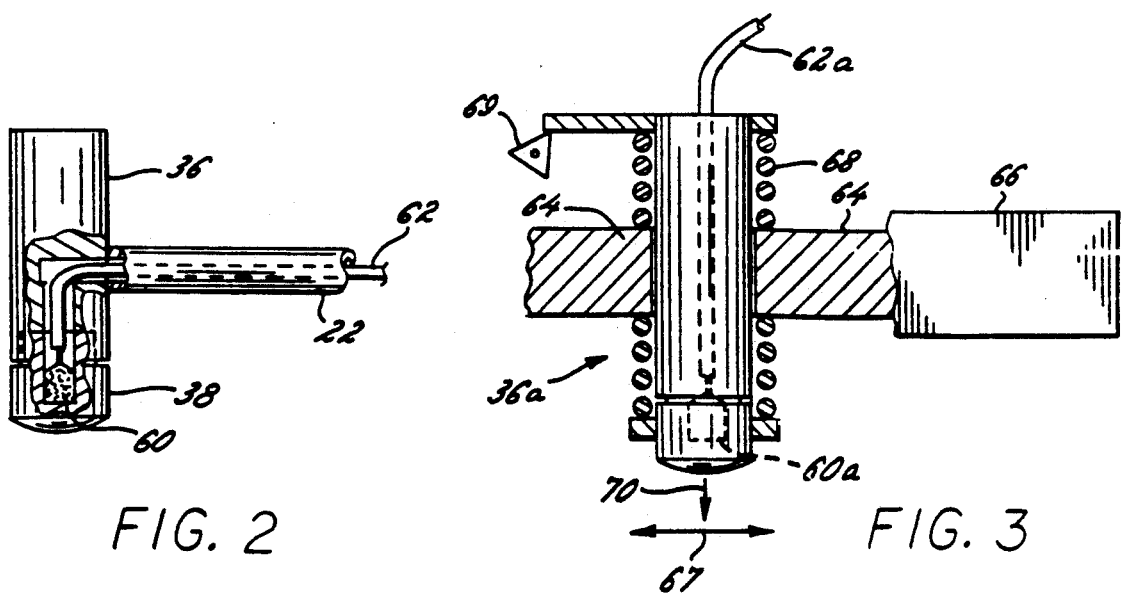
FIG. 2
FIG. 3

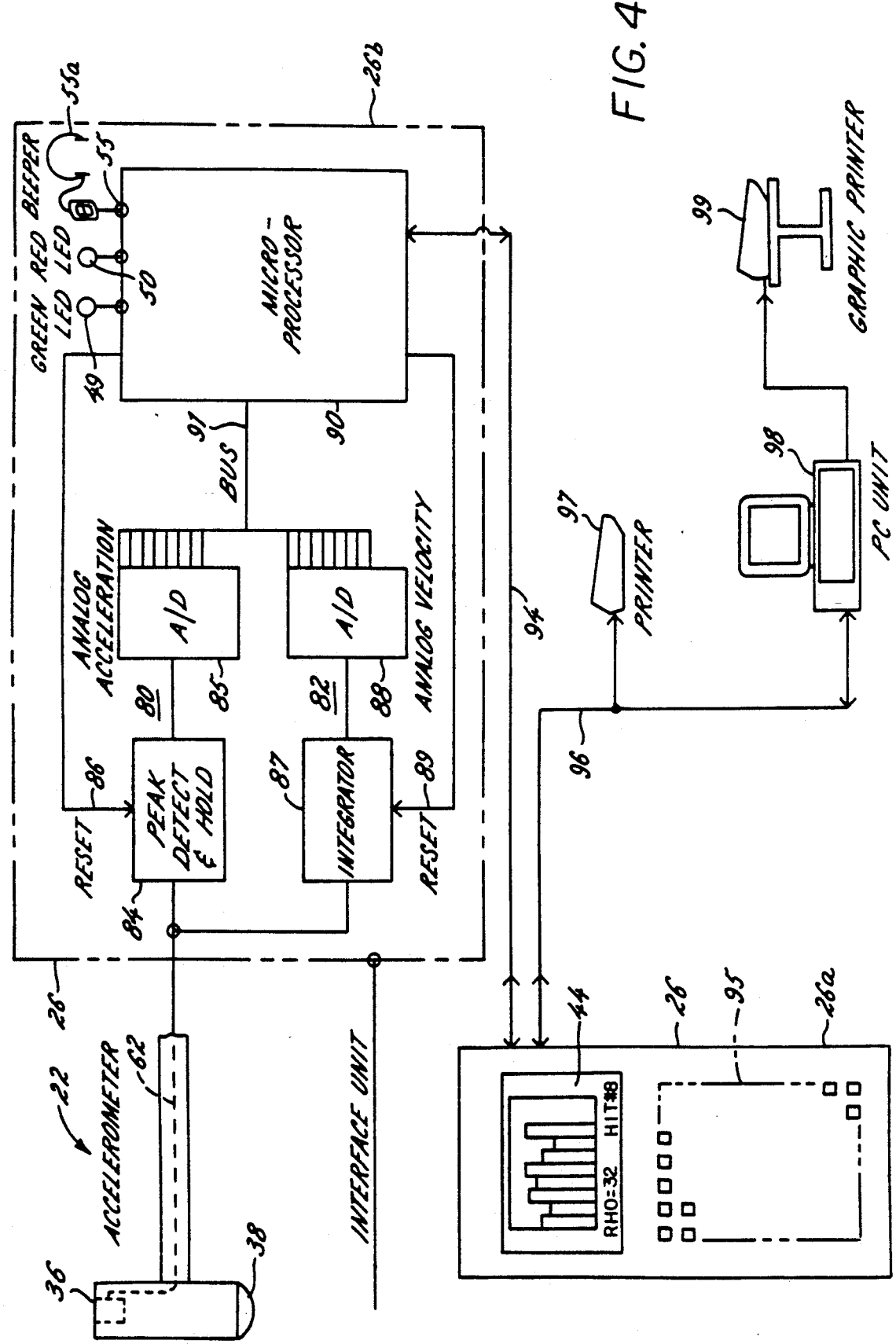

METHOD AND APPARATUS FOR QUANTITATIVELY EVALUATING ROLL HARDNESS

FIELD OF THE INVENTION

This invention relates to papermaking, and more particularly to a roll hardness tester capable of yielding repeatable and quantitative measurements of roll hardness.

BACKGROUND OF THE INVENTION

In papermaking, it is important that the hardness of the manufactured paper roll in the axial direction be maintained at a uniform level, since that is an indication of the uniformity of the overall manufacturing process. The reeled paper rolls on modern papermaking equipment can be on the order of 100 inches or more in diameter and from 200 to 300 inches or more in length. Even rolls which are slit and rewound for printing can be on the order of 40 inches or more in diameter and 36 to 72 inches in length. In order to gauge the uniformity of the manufacturing process, and also as a predictor of paper performance in printing, it is useful to test these paper rolls for hardness and hardness uniformity across the length of the roll.

A hand-held device which has long been used for such testing is described in Pfeiffer U.S. Pat. No. 3,425,267, and that device will sometimes be referred to herein as a Rho Meter. It utilizes the principal of measuring the peak deceleration value of a striker having a known mass, which is projected radially against the wound roll of paper from a fixed height under the impetus of a spring having a known spring constant. Thus, the '267 reference provides a reading for peak deceleration of a striker which impacts the wound paper roll with a known velocity. The hardness value is expressed in Rho units (derived from the Greek letter $\rho$ which is used to represent density), and is an arbitrary scale which has received rather wide acceptance in the papermaking industry. While the instrument does give repeatable results if used properly, it also presents a number of difficulties, particularly in high volume use.

It is extremely important in using the Rho Meter described in the '267 patent to assure that the instrument is perfectly aligned with the roll of paper to be tested, such that the runners on which the device contacts the paper are exactly tangent to the paper roll at the centerline of the striker. If the runners are not tangent to the roll, or if the tangent is located otherwise than at the striker centerline, the force of the striker will not be perpendicular with respect to the paper roll, and the expected velocity of impact will not be achieved, resulting in erroneous readings.

A further difficulty with the '267 device is the fact that a spring-type mechanism controls the impact of the striker against the roll, and the force exerted by the mechanism is, in part, related to the speed at which the trigger of the device is actuated. Thus, a user must pull the trigger slowly and at a consistent speed in order to get reproducible results from reading-to-reading and day-to-day.

Because the system utilizes a spring driving a mass, it is orientation sensitive. In the preferred mode, the device must be used with the striker motion precisely vertical, to eliminate velocity variations due to gravity effects on the weight. Thus, the ability to use the device consistently and according to its intended operating mode presupposes that the operator has access to the very top of the paper roll. That may not be difficult when testing 40-inch rolls, but when the rolls of paper are six, eight or more feet in diameter, taking of readings in the expected instrument orientation can become a problem.

Finally, while the '267 device is configured to latch the reading from the last test on an analog meter which is an integral part of the instrument. A commercial version of that instrument has also been configured with an analog jack for driving a strip chart recorder or the like, so that the operator can take a number of readings and produce a strip chart type roll profile without the need for manually recording the Rho numbers. While that does present a measure of convenience, the operator must still exercise care in the manipulative steps discussed above, in order to assure a constant force hit. The strip chart record is also substantially less useful than a complete set of readings which can be graphed or otherwise statistically analyzed.

A roll hardness testing device which does not suffer from many of the manipulative limitations of the '267 device is the simple backtender's stick. That device is a hardwood stick which the backtender's stick (the operator at the reel end of the papermaking machine) uses to strike the roll of paper and gauge (usually by both ear and touch) the frequency and amplitude of the resulting vibrations. The operator attempts to strike the roll with a predetermined force, and the sound produced by the backtender's stick hitting the roll (as well as the vibrations in the roll felt by the hand of the operator) are interpreted subjectively by the operator as a measure of roll tightness. That procedure is obviously very prone to inaccuracies introduced from operator-to-operator or even by a given operator over the course of a day. The technique is not known to be quantitative in any reasonable sense of the word.

SUMMARY OF THE INVENTION

In view of the foregoing, it is a general aim of the present invention to provide a method and apparatus for testing the hardness of materials, such as wound paper rolls, which can be as easy to manipulate as the backtender's stick but which provides repeatable quantitative information not subject to the vagaries of operator performance.

In that regard, an object of the present invention is to provide an electronic roll hardness testing device which can be manipulated like a backtender's stick, but which provides a repeatable quantitative measure of roll hardness.

According to an aspect of one embodiment of the invention, an objective is to provide a quantitative measure which correlates directly with Rho units or other such units of measure, which have or may become accepted in the papermaking industries.

According to a further aspect of the invention, an object is to provide a roll hardness testing device which facilitates the hardness profiling of rolls, leaving an operator free to manipulate the device which automatically collects and correlates information needed to produce a roll hardness profile.

In that respect, an object of the present invention, is to indicate to an operator after an impact of the striker one of two conditions—either that the strike was acceptable for taking a hardness reading or that conditions were unacceptable and the prior point should be repeated.

It is a significant object of the present invention to allow for differences in the force of the impact of the striker against the roll, without compromising the repeatability of the quantitative results. Even where the striker is configured for substantially repeatable force from strike to strike (e.g., a spring loaded striker), the normalization of the system output for variation in strike force is useful in eliminating the need for mechanical calibration of individual units across a family of units which may have different strike forces.

Thus, there is provided in accordance with the invention, a hardness tester for determining the relative hardness of a material, the tester comprising a striker for impacting the roll and producing an acceleration signal relating to the impact. Two signal types are derived from the acceleration signal. A first signal type relates to the peak deceleration during the strike. A second relates to the energy of the strike (a quantitative measure of the force of the hit). These two signals are coordinated in a computation means which produces a response indicating the hardness of the material in units which are independent of the energy of the strike.

It is a feature of the invention that the striker can be as simple to manipulate as the backtender's stick, being configured in the shape of an ordinary hammer, and used by the operator to simply tap along the roll at selected points to generate a hardness profile.

In that respect, it is a further feature of the invention to provide automatic means in combination with such a hardness tester, such automatic means serving to acquire each reading as the operator strikes the roll, and to signal the operator if the signals generated during any strike were unacceptable for generating a profile point for that strike. Thus, such a system has the capacity for generating a roll profile in a matter of seconds by the operator simply moving along the roll and tapping the roll at selected points, with each tap serving to generate a hardness point for the profile along the roll.

Other objects and advantages will become apparent with reference to the detailed description when taken with the following drawings in which:

BRIEF DESCRIPTION OF THE DRAWINGS

FIG. 1 is a perspective view showing two elements of a roll hardness tester exemplifying the present invention, namely the hand-operated striker and the associated portable computer;

FIG. 2 is a diagram showing the operating end of the striker with integral accelerometer;

FIG. 3 is a diagram illustrating a similar striker but adapted for automatic traverse of the paper roll to be measured;

FIG. 4 is a block circuit diagram exemplifying a roll hardness testing system constructed in accordance with the present invention;

Figure 5A:
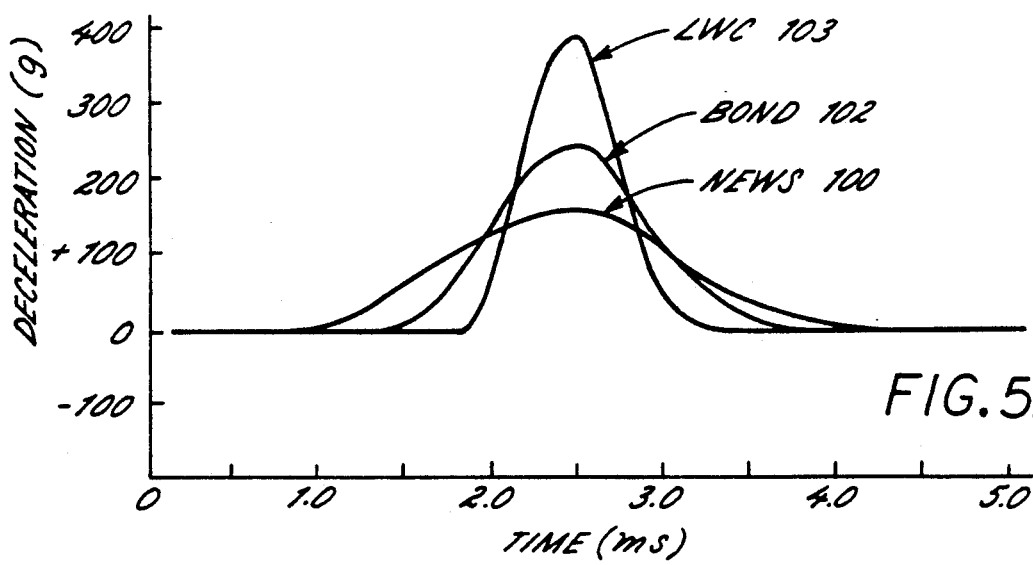
FIG. 5A-5B are graphs illustrating differences in accelerometer output occasioned by differing roll hardness and differing impact force.

While the invention will be described in connection with certain preferred embodiments, there is no intent to limit it to those embodiments. On the contrary, the intent is to cover all alternatives, modifications and equivalents included within the spirit and scope of the invention as defined by the appended claims.

DETAILED DESCRIPTION OF THE PREFERRED EMBODIMENTS

Turning now to the drawings, FIG. 1 illustrates two of the elements of a system constructed in accordance with the invention, such elements being those which are involved in acquiring hardness measurements. The system 20 includes a "probe" 22 which is a hammer-shaped device adapted to be hand-held and used by the operator to strike the roll. Electronic elements within the probe 22 are coupled by means of cable 24 to an associated hand-held (or belt clipped) calculator or computer 26. In the case where all of the driving electronics for the probe are not included in the probe itself, such additional electronics, as well as other display and control electronics, are included in the auxiliary unit 26.

It is seen that the probe 22 is constructed very much like a hammer and includes a handle portion 32 padded for gripping by the operator, and a neck portion 34 connecting the handle 32 to a head 36. The striker end 38 of the head 36 is rounded as at 40 so that it can impact a paper roll without the danger of substantially damaging the roll or tearing the paper.

In practicing the invention, and as will be described in greater detail below, an accelerometer is mounted within the head 36 so that it is excited whenever the operating end 38 of the head 36 strikes a paper roll. The accelerometer produces signals which are analyzed both for peak deceleration and also for energy content, such information being utilized to provide a measure of roll hardness which is independent of the force of the strike used to generate the signals. It is noted that the preferred embodiment of the invention utilizes an accelerometer, and integrates the acceleration signal to get a measure of velocity which is directly proportional (for a constant mass) to the impulse force. Thus, in its broadest aspects, the invention need not be limited to use of an accelerometer as the signal producing transducer, or to integration of a particular type of signal to get a measure of the energy or force of the strike. As one example, it is possible to utilize a force transducer in the head of the probe, and scale the output of the force transducer to produce a signal similar to that taken from the accelerometer in the preferred practice of the invention. As an alternative with respect to signal processing, the signal used to normalize the peak deceleration signal is described generally as a signal relating to the force of the strike. In its preferred mode, that signal is most conveniently obtained by integrating the acceleration signal which produces a signal relating to velocity. And velocity at a constant mass is related to force impulse, which in turn is a measure of the energy in the impact. In any event, when a broad term such as signals relating to the energy of the impact is used in this application, it is intended in its broadest sense as encompassing any of the various alternatives for sensing of signals from the head to produce a measure relating to the force or energy of the strike.

Referring again to FIG. 1, it will be appreciated that an operator simply needs to grasp the handle 32 of the probe, and swing it, much as a standard hammer, to impact the roll. It is a relatively simple matter for the operator to choose the desired point of impact, then to assure that his swing is such that the point of impact will be normal to the roll surface at the desired point. The difficulty, however, can arise in assuring that the force of the hit is the same every time, and the circuit means associated with the probe are adapted to make such a consideration irrelevant. All that is required is force within a predetermined range (greater than the minimum necessary to produce a signal capable of being measured, and less than the maximum which would tend to overload or saturate the circuitry). A force which produces signals anywhere within that desirable range will then produce the two aforementioned signals, one relating to peak deceleration and the other to impulse force of the impact, and those can be used to determine the hardness of the roll which has caused the deceleration of the probe upon impact with the roll.

As noted above, the probe 22 is connected to the portable calculator unit 26 by means of cable 24. In the illustrated embodiment, the majority of the electronics are carried in the portable computer 26, but this is of course unnecessary to the practice of the invention. In the exemplary embodiment, the calculator 26 is a substantially rectangular device, approximately equal in size to the conventional hand-held calculator, and preferably having a belt clip so that, if desired, the device can be simply clipped to the belt while a series of measurements is taken. However, the device is clearly small enough that it can also be held in one hand while the operator uses the other to strike the roll at the desired number of places in order to take a roll profile.

A connector 41 provides for connecting of the probe 22 to the calculator. It is seen that the case 42 is provided with a display 44, in the illustrated embodiment an LCD display. The LCD display 44 is particularly configured for roll profiling, and has an upper section for displaying a bar chart 46 showing the hardness profile across the roll. The lower section of the LCD display 44 includes a left-hand portion for display of numeric characters 49 which indicate the Rho number of the previous measurement, and characters 50 which indicate the number of the hit in the profile being taken.

In the preferred embodiment, the system includes a pair of indicators shown as LED's 51, 52 mounted in the case 26. Of course the indicators could be mounted in the probe, if preferred. LED 51 is preferably a red LED which is illuminated to indicate that the signals taken from the prior reading were not adequate to calculate a Rho number for that reading. Thus, lighting of the LED 51 indicates to the operator that another sample of the previous point should be taken. The LED 52 is preferably green and, when flashed, indicates that the readings that the instrument has just taken were acceptable for calculating a Rho number, i.e., that the operator can go on to the next hit.

For the sake of completeness, it is also noted that the computer unit includes a power switch 54 which powers the electronics in both the probe 22 and the computer 26. An array 95 of input switches is sensed by an internal microprocessor to allow the operator to communicate with the system. One of such switches can, for example, be used as a switch to signal the start of a roll profile operation, instructing the electronics that a series of signals for a given roll will be forthcoming. Others of the switches can be utilized, for example, to cause the internal microprocessor system to perform a statistical analysis on the collected data. In the currently preferred practice of the invention, the front panel of the calculator 26 is a commercially available computing device which includes the input array of switches, the display, the microprocessor capacity for driving those elements and performing other computer operations, and standard communication ports for communicating with other devices. Self-contained batteries, typically maintained in the computer unit 26, are preferably of the rechargeable variety. The computer 26 also has a connector 55 which allows for connection by way of a cable 56 to a set of headphones (not shown in FIG. 1). The headphones are a convenience to the operator and are adapted to beep to alert the operator whenever a reading has been attempted but the signals were inadequate to derive a Rho number measurement.

With that understanding of the system of FIG. 1, it will be appreciated that an operator is now provided with the capability for easily and directly making a large number of measurements of paper rolls, be they large newly manufactured reels, or smaller rolls slit for printing. It is a simple matter for the operator to approach the roll, then strike the paper roll directly with the rounded end of the hammer-like probe. The computer will automatically take signals from the self-contained accelerometer to compute a measure of the roll hardness for the point impacted. The operator need only strike the roll at the desired number of locations determined by the quality control procedure: for example, every several inches along the length of the roll. The computer has the capability, as has been described above, to keep track of the number of hits during a profile and a running tally of the hardness magnitudes for each hit. That data, as will be described in connection with the circuit diagram below, is maintained in a memory internal to the computer 26. The operator has the option to connect a peripheral printer (not shown) to the computer 26 for printing out of the profile or individual readings thereof. As an alternative, the computer 26 is provided with a conventional communication port (such as an RS232 port) so that it can be interfaced directly to a another device.

In any event, it will be clear that the quality control checks are not only rapidly performed, but with much less chance for error. The operator need only be sure that he is approaching the rolls in a proper sequence, and that when the system is set for the profile of a given roll, all readings be taken of that same roll. Then simply by marching down the roll, and striking the roll at the appointed positions, the operator causes the system to acquire the necessary information, make the necessary computations, and signal the operator if any readings need be repeated. When the entire procedure is completed for as many rolls as need be checked, the operator can then either print out the necessary information using the peripheral printer, or put the acquired information into the plant quality control computer for processing and display as required. The advantage over the old backtender's stick method on the one hand or even the Rho Meter on the other, will now be apparent. The backtender's stick approach gives the operator a qualitative feel for the tightness of the rolls, but no quantity to record. The Rho Meter gives the operator quantitative information, but that information was subject to some error because of the difficulty of using the instrument, and also was inconvenient to use to record roll profiles with adequate information content.

With that understanding of system structure and operation, attention will now be directed to additional details of the individual elements and their relationships when configured in the practice of the present invention. FIG. 2 shows, in partly schematic form, the operating head 36 of the striking probe 22. Inside the striker is mounted an accelerometer 60 having lead wires 62 which extend from the accelerometer through the handle 22 for coupling by means of the interconnecting cord 24 to the hand-held computer 26. The details of the accelerometer 60 mounting are not illustrated. Suffice it to say that the accelerometer is mounted such that when the rounded head end 38 impacts an external mass (such as by striking a roll), the deceleration imposed on the head 36 causes a proportional signal to be produced in the accelerometer 60 and coupled by means of wires 62 to remaining circuitry, for an indication of the acceleration (or deceleration) of the head during a strike.

Digressing briefly to FIG. 3, there is shown an alternative striker head 36a mounted for mechanical traverse across a roll to be measured and for automated impacting against the roll. It is seen that the modified head 36a is mounted on a guide rod 64, and is driven by means of traversing mechanism 66. The striker with enclosed accelerometer 60a can thus traverse the roll in the direction generally indicated by the double-headed arrow 67. A spring mechanism 68 loads the modified head 36a to a position displaced from the roll by compression of the spring; release of a trigger mechanism 69 serves to release the head 68a in the direction indicated by arrow 70 to impact the roll and thereby produce a signal in the accelerometer 60a for coupling by means of wires 62a to electrical circuitry for analysis. The system of FIG. 3 can be configured to produce a relatively constant force strike from cycle to cycle. However, it is preferred that the circuitry coupled to the accelerometer be of the type described herein to compensate for variations in force of the strike which might be caused by variations in release of the trigger mechanism, changes in the mechanical loading system over time, weakening of the spring, and the like so that even though the strike force is substantially the same over time, any minor differences in that strike force from reading to reading will be compensated. It will at first appear that the strike force compensation, which is of great importance to the hand-held system of FIG. 2, will be of lesser importance in the mechanized version of FIG. 3, insofar as reading-to-reading uniformity is concerned. However, the importance of the compensation techniques, even in connection with the mechanized system, will be further appreciated when it is realized that even in the mechanized version the systems need not be mechanically calibrated to be identical to each other or to some fixed standard, in order to produce readings which are accurate with respect to a given scale. Such calibration will be obtained by modifying the peak deceleration signal by means of a further signal related to the force impulse of the strike, and that normalization will tend to produce readings referenced to a fixed scale rather than some arbitrary and uncalibrated scale unique to a particular mechanism or particular spring constant.

FIG. 4 shows the electrical and electronic interrelationship between the elements of a system constructed in accordance with the present invention. In the upper left-hand portion of the drawing, there is shown the striking probe 22 including head 36, having a rounded striking end 38 and containing an internal accelerometer 60. The accelerometer is connected by means of cable 62 to additional electronic circuitry, preferably contained in the case of the hand-held or portable calculator 26. FIG. 4 shows the preferred embodiment of the invention wherein the calculator or computer 26 comprises two elements, a processor based unit 26a, in the form of a self-contained computer which includes input switches, display, microprocessor, memory, and the elements necessary to do significant programmed processing, and a second specialized electronics section 26b which serves to collect and preprocess signals from the striking probe. It will be apparent, however, that a single processor of adequate capacity and with adequate memory can be configured to perform both functions.

Turning to the circuitry for processing signals originating in the probe 22, it is seen that the internal circuit elements establish two paths 80, 82 for signal flow within the electronics. The path 80 is provided for processing signals relating to peak deceleration during a strike, while the second path 82 is provided for processing signals relating to the force of the strike. The force related signals are conveniently processed in the form of impact energy signals which, as will be described below, are determined from the time integral of the deceleration signal during a strike. Thus, the signal from the accelerometer 60 is provided to the circuitry by means of cable 62 and is branched to the two paths 80, 82 (in the preferred embodiment), the first path maintaining a record of peak deceleration during the strike, and a second path 82 maintaining a record of the time integral of deceleration as a measure of the energy (or impulse force) of the strike. When the signals in the former path 80 are normalized by those in the second path 82, it is found that repeatable quantitative results are obtained for rolls of the same hardness, irrespective of the force of the strike within a relatively large range of acceptable striking force.

The first signal path 80 includes a peak detect and hold circuit module 84 having an input coupled to the accelerometer and an output coupled to an analog-to-digital converter 85. The peak hold and detect circuit 84 can be configured as a sample and hold circuit which has an input continually driven higher whenever a higher input signal is presented, but which does not discharge until reset by means of a signal on line 86. It is seen that the line 86 is driven by a microprocessor 90 and serves to reset the peak detect and hold circuit 84 prior to the initiation of a data acquisition cycle during the course of a measurement.

The second channel 82 includes an integrator 87, preferably in the form of an analog integrator having output which feeds an analog-to-digital converter 88. If desired, the analog-to-digital converters 85, 88 can be configured as a single device time shared among the two channels 80, 82. The integrator 87 is preferably a high precision operational amplifier arranged with capacitive feedback to provide a precision integration of the signal received from the accelerometer during a strike. It is also seen that the integrator 87 has a reset input 89 driven by the microprocessor 90. Conveniently, both the integrator 87 and the peak detector 84 can be reset by the microprocessor (on their respective lines 86, 89) in preparation for striking of the roll to generate a new reading. Preferably, the reset is applied after the accelerometer signals are quiescent for a given time (quiescent in the sense that they are below threshold) indicating that the prior strike has been completed. As an example, after signals are detected in the input circuitry 84, 87 and digitized in the converters 85, 88, the digitizers upon indicating a completion of the digitization process can produce a reset signal which is processed by the microprocessor to reset the input circuits 84, 87 in preparation for the next strike.

It is also noted that the input circuitry 84, 87 preferably includes a threshold establishing means, with the threshold set sufficiently high to maintain the circuit in the inactive condition while the accelerometer is being moved or even swung, but with the threshold set sufficiently low that it will be rapidly exceeded when the probe impacts the roll. Thus, the operator is allowed to swing the probe 22 toward the paper roll without causing the detecting electronics to be affected by the resulting acceleration. However, the threshold is set in such a way that the accelerometer signals occasioned by the initiation of impact are above the threshold, and therefore sensed.

It will be apparent to those skilled in the art that subtle differences in the mode of operation of the system are easily provided by appropriate programming of the microprocessor 90 which utilizes the bus structure shown (as well as other connections implicit in the illustration) to control the input circuitry, the converters, the operator interface indicators, the display and peripheral devices, and all other aspects of system operation. Thus, the microprocessor 90 has a major input/output bus 91 which is coupled to both analog to digital converters 85, 88 for receiving digitized inputs therefrom. It will be recalled that the digitized input received from the analog-to-digital converter 85 is that relating to acceleration, whereas that received from the converter 88 is that related to force impulse or velocity. The manner in which those signals are utilized to provide an output in consistent and repeatable units will be described in connection with FIGS. 5 and 6. However, before turning to those figures, it will be noted that the microprocessor 90 has connected thereto the light emitting diode indicators 51, 52 and headphones 55a (connected to the system by means of connector 55) which were described as operator interface aids in connection with FIG. 1. Thus, the microprocessor 90 is programmed to illuminate the green LED 52 whenever a good reading has been taken, the red LED 51 whenever a previous reading has been determined to be out of range, and to send tones to a headset 55a to indicate progress to an operator taking a reading, series of readings or roll profile.

FIG. 4 also illustrates a pair of communication ports, preferably in the form of commercially available RS232 ports, although other forms of communication connections can be used if desired. The first of such ports 94 is connected between the microprocessor 90 and the computer portion 26a (which includes liquid crystal display 44, and the array 95 of switches). Depression of switches in the array 95 causes signals to be coupled to the microprocessor internal to the computer device 26a, or in the case where only a single microprocessor is utilized, to the single microprocessor 90 which drives both devices. The microprocessor 90, having determined results from prior or current strikes, is also able to communicate information on the communication bus 94 to drive the display 44, or, in the embodiment with a self-contained processor in computer 26a, the internal processor can drive such display. The display 44 is shown to include the bar graph indicating roll profile (mentioned in connection with FIG. 1) as well as the Rho number for the current hit and hit number for the current hit then being processed.

A second RS232 communication port 96 is also provided for connection between the hand-held computer device 26 and additional peripheral equipment including the aforementioned portable printer (shown in FIG. 4 as printer 97), conventional personal computer 98 and a computer-driven printer 99. As noted above, the portable printer 97 can be driven directly from the computer 26a to produce a listing of test results almost immediately. The information for the current roll profile (as well as previously stored roll profiles) can also be communicated on the bus 96 to a standard personal computer 98 so that additional statistics or processing routines can be run on such data, the data displayed on the screen of the personal computer in conventional fashion and also printed out at 99 when desired.

Figure 5B:
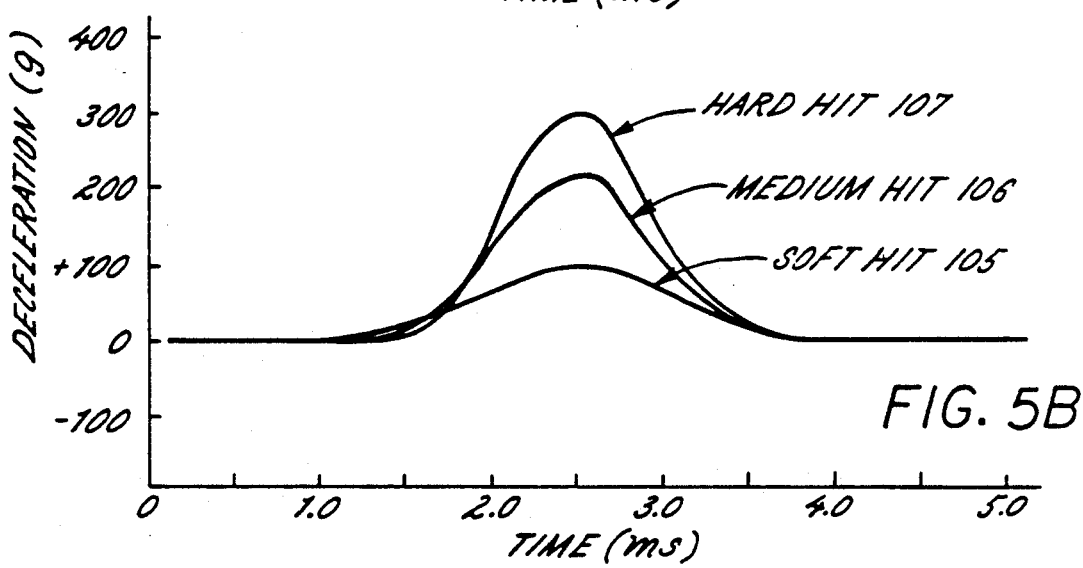

Turning now to FIGS. 5a and 5b, there is illustrated an aspect supporting the use of the two sets of signal channels 80, 82 of FIG. 4, and the manner in which the maintenance and combination of the two types of information serves to render the system insensitive to changes in force of the strike used to take any reading in a particular set. More particularly, FIG. 5a illustrates the accelerometer signal with respect to time under conditions of constant strike force but for materials of different hardness. It is seen that a first curve 100 has a maximum deceleration peak well below 200g (representing a relatively soft material such as newsprint), an intermediate curve 102 peaked at slightly over 200g (representing material of intermediate hardness such as bond), and a third curve 103 sharply peaked above 300g (representing a harder material such as a highly calendared stock). It is also seen that the softer materials have deceleration characteristics which have broader bases, and that the harder materials provide not only higher peaks, but shorter deceleration times. Thus, as a general rule, it can be seen that as the hardness of the object increases (at a constant strike energy), the deceleration peak increases and the contact duration decreases. However, when the further variable of strike energy is introduced, it will not be possible to simply use peak and duration information to distinguish between the types of material.

That fact is illustrated in FIG. 5b which shows the response of material of a given hardness for strikes having different energies including a soft hit illustrated at 105, a medium hit at 106, and a hard hit at 107. It is seen that the contact duration for the three hits is about the same (primarily a function of material hardness), but that the value of the peak deceleration differs substantially, ranging from below 100g for the soft hit to approximately 300g for the hard hit. It will thus be appreciated that if hits of differing magnitudes such as illustrated in 5b were applied to the materials of differing hardness as illustrated in FIG. 5a, it would not be possible to readily distinguish (much less quantify) the hardness differences in the materials.

In accordance with the invention, the area under the curves of FIG. 5b is determined (in the channel 82 of FIG. 4) to provide a measure of the impact energy and thus allow the peak information from channel 80 to be normalized for impact energy, resulting in a quantitative energy independent measure of relative roll hardness. Integrating the curves of FIG. 5b is equivalent to integrating an acceleration curve during the impact. Integration of the acceleration thus produces an output indicative of velocity, and such time integral produces what is known as the force impulse, a measure of the energy expended by the striker in impacting the roll.

It will thus be appreciated that the channel 82 of the FIG. 4 circuitry integrates the signal produced by the accelerometer over time during the course of a strike, with the result being the integration of the strike impulse as shown in FIG. 5b. It will be appreciated that a comparatively smaller integrated magnitude will be produced with soft hits as exemplified by curve 105, whereas a substantially higher magnitude will be produced as a result of hard hits as exemplified by curve 107. It will also be appreciated that when the circuit is configured with a lower limit threshold (such as 100 millivolts) equivalent in one embodiment of the invention to an acceleration of 10g, no substantial error is introduced because of the symmetry of the curve and the resulting ability to make adjustments for such a threshold.

Referring again briefly to FIG. 5a, while a family of curves relating to different strike forces for each of the materials of different hardness has not been provided, a mental comparison of FIGS. 5a and 5b will suggest that when the peak reading illustrated in FIG. 5a is modified by a signal relating to the area under the selected curve of FIG. 5b, output will be produced which is independent of the strike force, and thus has been normalized for the strike force differences illustrated in FIG. 5b.

Figure 6:
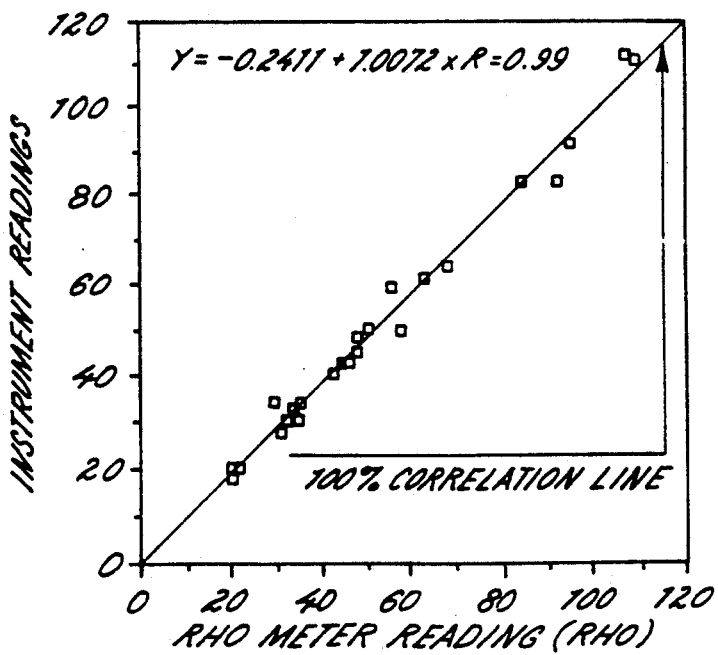
FIG. 6 is a diagram illustrating a correlation between the output reading of an exemplary instrument constructed in accordance with the present invention and an arbitrary but accepted Rho scale of roll hardness.

The result of that normalization is illustrated in FIG. 6, which is a graph illustrating roll meter readings on the Rho Meter (i.e., the meter readings from the prior accepted device illustrated in the '267 patent) vs. "instrument readings", i.e., readings made by a system as illustrated in FIG. 4 and exemplifying the present invention. The linear equation in the upper left-hand corner of the graph is the mathematical expression which relates instrument readings (y's) to Rho Meter readings (x's). Thus, it is seen that the relationship is substantially linear with a value for R of about 0.99.

In a particular embodiment of the invention, a relationship was derived relating Rho Meter reading to the velocity and acceleration information obtained in channels 80, 82 of the circuit of FIG. 4. That relationship is described by the following equation:

$$Ln(Rho) = C_1 * Ln(V) * ln(V) + C_2 * Ln(A) * Ln(A) + C3$$

For range on A and V (binary) of:

$$40 < A < 254, 40 < V < 254$$

Where:
Ln(Rho) = Natural Log Rho Hardness
Ln(V) = Natural Log Binary Velocity
Lv(A) = Natural Log Binary Acceleration
$C_1 = -0.147075 +/- 0.000687$
$C_2 = 0.128536 +/- 0.000649$
$C_3 = 4.263272 +/- 0.013729$ For the particular instrument tested, the model illustrated by the foregoing equation had a correlation coefficient of 0.987. The agreement between an instrument constructed in accordance with the teachings of this invention and the Rho Meter readings taken using techniques long accepted, will now be apparent. It will also be noted, however, that if the particular hardware configuration is altered, the specific relationship between meter output and the signals in channels 80, 82 will need to be determined empirically for that particular hardware configuration. Generally, however, a relationship like that set out in the aforementioned equation will be derived for a particular hardware configuration, and can be repeatedly used in generating quantitative information scaled to a known standard.

It was noted above, and it will be re-emphasized here now, that a complete understanding of the invention has been conveyed, that the invention provides the opportunity to generate highly accurate (and reasonably highly compacted) sets of data for paper rolls at any desired time in the manufacturing or utilization sequence. It is simply necessary to dispatch an operator with the elements of FIG. 1 to the area where the rolls are stored, and with instructions for which of the rolls are to be tested, in which sequence, and with how many hits per roll.

With that information in hand, the operator need only initiate each roll profile measurement sequence by depression of an appropriate pushbutton on the calculator 26. The operator then need only strike the roll at desired locations for the number of hits assigned to that profile. The system will continue to indicate to the operator (by flashing LED's, tones in the headset or otherwise), whether each reading is acceptable and whether any should be repeated. In a matter of seconds, the operator will have sufficient information stored in the calculator device 26 relating to the profile of the entire roll, following which he can hit a reset button to initiate a data acquisition cycle for the next roll, and proceed as with the prior roll. In a matter of a few minutes, a relatively unskilled operator can progress through a number of rolls of manufactured paper and return the calculator to the quality control department, where the data can be input into the standard quality control computer system for analysis and processing, providing data which is not only substantially more accurate than could be collected in the past, but which is also potentially greater in volume and in processability, allowing paper manufacturers previously unrealized opportunities to optimize the production process.

What is claimed is:

1. A hardness tester for determining the relative hardness of a material, the tester comprising, in combination;
    a striker for impacting the material with force which can vary within a prescribed range, and producing acceleration signal relating to the impact,
    first means for producing a first signal relating to the energy of the striker impact, said first signal relating to the force of the particular impact,
    second means for producing a second signal relating to the peak deceleration of the striker, and
    computer means for processing the first and second signals, such means using information derived from the first signal to correct the second signal, the result of the correction being a quantified output indication of the relative hardness of the material, the output being substantially independent of the force which produced the impact.

2. The combination as set forth in claim 1 wherein the computer means further comprises correlating means for correlating the quantified output to units of a predetermined hardness scale, and indicator means for indicating the material hardness in said units.

3. The combination as set forth in claim 2 wherein the units of the predetermined hardness scale are Rho units.

4. The combination as set forth in claim 1 wherein the striker comprises a hammer-shaped head affixed to a handle to produce a hand-held hammer-like device which can be wielded by an operator like a conventional hammer.

5. The combination as set forth in claim 4 wherein the striker includes an accelerometer for producing the acceleration signal.

6. The combination as set forth in claim 5 including threshold means associated with the acceleration signal having a threshold level below acceleration signals resulting from swinging of the hammer-like device, but to be exceeded upon impact.

7. The combination as set forth in claim 1 further including housing means positioned for traverse across the material to be tested, means for mounting the striker within the housing means in a position juxtaposed to the material, and means for causing the striker to impact the material during traverse of the housing to take a plurality of readings therealong.

8. The combination as set forth in claim 1 wherein the material is in roll form, and the hammer-like device is adapted for tapping along an axial line of the roll in an orientation substantially radial with respect to said roll.

9. A method for determining and indicating the relative hardness of a wound roll, the method comprising the steps of:
impacting the roll with a striker with a force which can vary within predetermined limits,
determining the impulse force of the strike,
determining the peak deceleration of the striker during the strike.
combining information relating to the impulse force of the strike and the peak deceleration during the strike to determine a quantitative measure of hardness for the wound roll at the point of strike, and
displaying the roll hardness quantity.

10. The method as set forth in claim 9 wherein the process further includes the step of correlating the quantitative roll hardness measure to a predetermined Rho hardness scale, and wherein the step of displaying includes displaying the roll hardness quantity in terms of said Rho hardness scale.

11. The method as set forth in claim 10 wherein the method further comprises the steps of impacting the roll at a plurality of selected points with strikes which need not be of the same force, and computing comparable Rho units for each strike to produce a profile of roll hardness in Rho units which are comparable due to compensation for differences between the forces causing the respective strikes.

12. The method as set forth in claim 9 wherein the step of impacting further comprises swinging a hammer-shaped probe so that a hammer-shaped head of the probe impacts the roll in a substantially normal direction with respect to the roll surface.

13. The method as set forth in claim 9 wherein the steps of determining comprise measuring the impact with an accelerometer.

14. The method as set forth in claim 13 wherein the step of determining the energy of the strike comprises integrating the signal from the accelerometer with respect to time.

15. The method as set forth in claim 13 wherein the step of determining the deceleration comprises detecting the deceleration signal from the accelerometer.

16. The method as set forth in claim 14 wherein the step of determining the energy impulse force further comprises the step of imposing a threshold at a level sufficiently high to overcome accelerometer signals generated by swinging of the hammer-like device, but sufficiently low to detect accelerometer signals resulting from the strike.

17. A method of profiling paper rolls comprising the steps of:
a) providing a hammer-shaped probe containing an acceleration sensor,
b) swinging the hammer-shape probed to impact the roll at a predetermined point to produce sensor signals relating to the deceleration of the probe resulting from the impact with the roll,
c) processing the deceleration signals to produce a quantitative measure of the roll hardness at the impacted point which is substantially independent of the force of the impact,
d) signalling to the operator whether the signals resulting from the impact were acceptable or unacceptable,
e) repeating steps b-d at the last impact point if the result was unacceptable,
f) storing the result of the measure of roll hardness for the impacted point if the result was acceptable, and
g) repeating steps b-f at additional impact points to produce an automatically stored roll profile acquired by tapping of the roll along its length with the probe.

* * * * *